(12) United States Patent
Droessler

(10) Patent No.: US 12,233,024 B2
(45) Date of Patent: Feb. 25, 2025

(54) METHOD FOR SEPARATING A HOLLOW GLASS BODY FROM A GLASS TUBE AS WELL AS METHOD AND SYSTEM FOR MANUFACTURING A RECEPTACLE

(71) Applicant: NIPRO CORPORATION, Osaka (JP)

(72) Inventor: Michael Droessler, Gehrden (DE)

(73) Assignee: NIPRO CORPORATION, Osaka (JP)

( * ) Notice: Subject to any disclaimer, the term of this patent is extended or adjusted under 35 U.S.C. 154(b) by 889 days.

(21) Appl. No.: 17/271,416

(22) PCT Filed: Aug. 29, 2019

(86) PCT No.: PCT/JP2019/033988
§ 371 (c)(1),
(2) Date: Feb. 25, 2021

(87) PCT Pub. No.: WO2020/050139
PCT Pub. Date: Mar. 12, 2020

(65) Prior Publication Data
US 2021/0347674 A1    Nov. 11, 2021

(30) Foreign Application Priority Data

Sep. 3, 2018 (DE) .................. 10 2018 006 961.4
Sep. 3, 2018 (DE) .................. 10 2018 006 968.1

(51) Int. Cl.
| | | |
|---|---|---|
| C03B 33/02 | (2006.01) | |
| A61J 1/06 | (2006.01) | |
| A61M 5/31 | (2006.01) | |
| B23K 26/0622 | (2014.01) | |
| B23K 26/08 | (2014.01) | |

(Continued)

(52) U.S. Cl.
CPC ............ *A61J 1/065* (2013.01); *A61M 5/3129* (2013.01); *B23K 26/0622* (2015.10); *B23K 26/0823* (2013.01); *B23K 26/38* (2013.01); *B23K 26/402* (2013.01); *B65B 3/003* (2013.01); *C03B 33/0222* (2013.01); *C03B 33/06* (2013.01); *A61J 1/05* (2013.01); *A61M 5/178* (2013.01)

(58) Field of Classification Search
CPC ........................... C03B 33/0222; C03B 33/06
See application file for complete search history.

(56) References Cited

U.S. PATENT DOCUMENTS

| | | |
|---|---|---|
| 5,782,815 A | 7/1998 | Yanai et al. |
| 6,310,318 B1 | 10/2001 | Vetter et al. |

(Continued)

FOREIGN PATENT DOCUMENTS

| | | |
|---|---|---|
| DE | 19616327 | 11/1997 |
| DE | 19904978 | 8/2000 |

(Continued)

OTHER PUBLICATIONS

Extended European Search Report issued May 23, 2022 in corresponding European Patent Application No. 19856918.8.

(Continued)

*Primary Examiner* — Cynthia Szewczyk
(74) *Attorney, Agent, or Firm* — Wenderoth, Lind & Ponack, L.L.P.

(57) ABSTRACT

A glass tube is treated with laser cutting for separating a hollow glass body from the glass tube. A laser beam used for laser cutting is focused on a wall of the glass tube.

20 Claims, 11 Drawing Sheets

(51) Int. Cl.
    *B23K 26/38*     (2014.01)
    *B23K 26/402*     (2014.01)
    *B65B 3/00*     (2006.01)
    *C03B 33/06*     (2006.01)
    *A61J 1/05*     (2006.01)
    *A61M 5/178*     (2006.01)

(56) References Cited

U.S. PATENT DOCUMENTS

| | | | |
|---|---|---|---|
| 2001/0009250 A1* | 7/2001 | Herman | C03B 29/02 |
| | | | 606/11 |
| 2001/0035447 A1* | 11/2001 | Gartner | C03B 33/09 |
| | | | 225/2 |
| 2010/0076375 A1 | 3/2010 | Alexandre | |
| 2012/0060558 A1 | 3/2012 | Haselhorst et al. | |
| 2014/0216108 A1 | 8/2014 | Wiegel et al. | |
| 2015/0114043 A1 | 4/2015 | Risch et al. | |
| 2016/0129526 A1 | 5/2016 | Russ et al. | |
| 2016/0272531 A1* | 9/2016 | Inayama | C03B 33/082 |
| 2017/0216972 A1 | 8/2017 | Pialot et al. | |
| 2018/0029918 A1 | 2/2018 | Hunzinger et al. | |
| 2018/0215648 A1 | 8/2018 | Wada et al. | |
| 2018/0215649 A1 | 8/2018 | Wada et al. | |
| 2021/0229848 A1 | 7/2021 | Nishizawa | |

FOREIGN PATENT DOCUMENTS

| | | |
|---|---|---|
| DE | 10 2010 045 094 | 3/2012 |
| DE | 10 2011 006 738 | 10/2012 |
| DE | 10 2012 101 948 | 9/2013 |
| DE | 10 2016 114 104 | 2/2018 |
| EP | 0 723 784 | 6/2003 |
| EP | 3 366 656 | 8/2018 |
| JP | 61-115853 | 6/1986 |
| WO | 2008/034960 | 3/2008 |

OTHER PUBLICATIONS

International Search Report issued Nov. 5, 2019 in International (PCT) Application No. PCT/JP2019/033988.
Extended European Search Report issued Jun. 30, 2022 in European Patent Application No. 19857556.5.
First Examination Report issued Sep. 6, 2022 in Indian Patent Application No. 202117008613.

* cited by examiner

Fig. 4
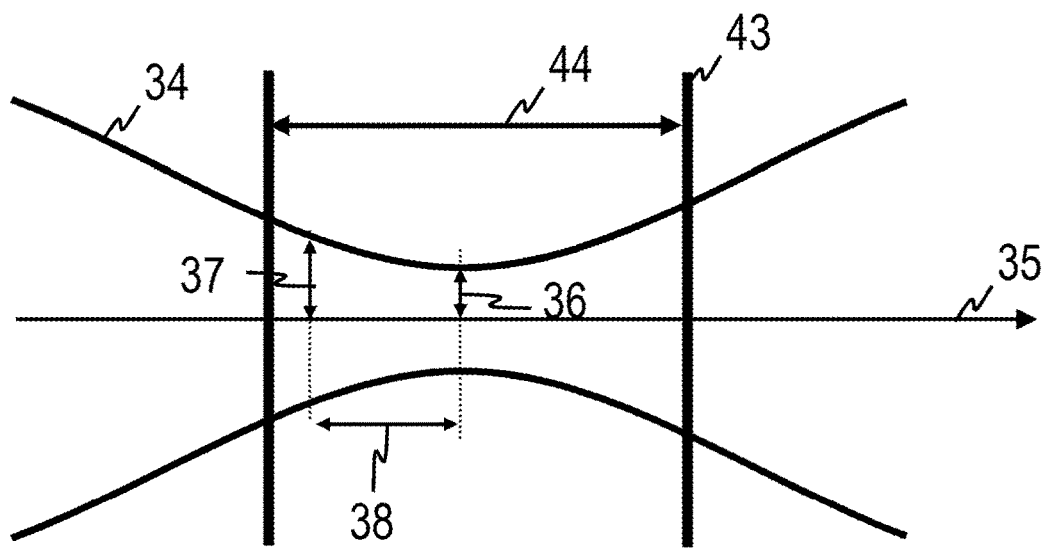
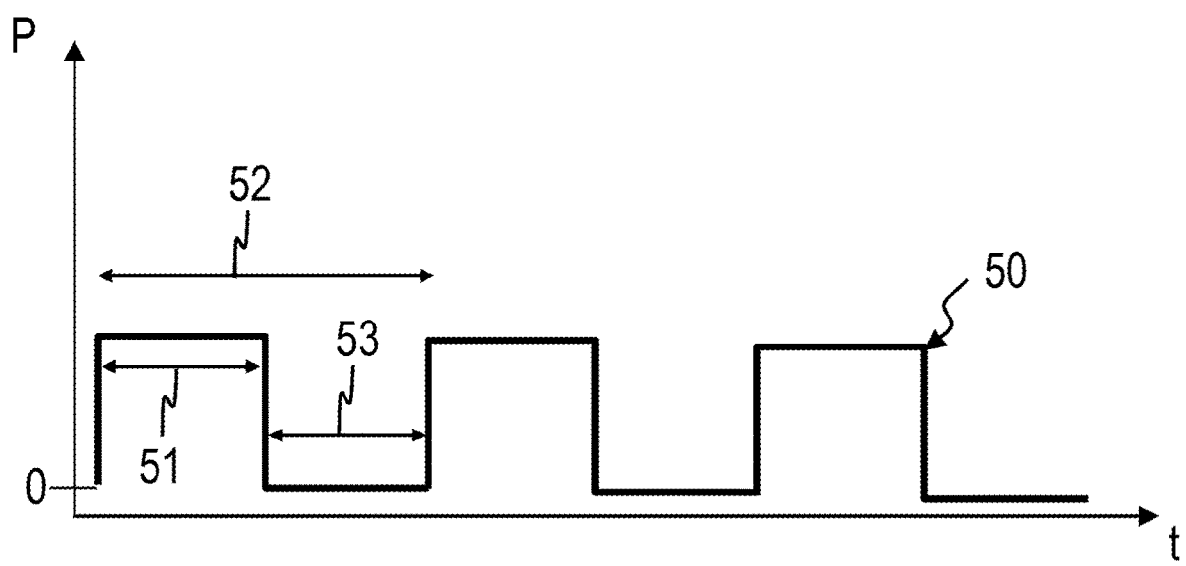
Fig. 5

METHOD FOR SEPARATING A HOLLOW GLASS BODY FROM A GLASS TUBE AS WELL AS METHOD AND SYSTEM FOR MANUFACTURING A RECEPTACLE

TECHNICAL FIELD

The invention relates to a method and system for separating a hollow glass body from a glass tube, in particular for manufacturing medical receptacles such as syringes or medical cartridges or for manufacturing other receptacles. The invention relates in particular to such methods and systems in which a hollow glass body is separated from a glass tube by using laser radiation.

BACKGROUND

Hollow glass bodies are used for manufacturing medical receptacles such as syringes or drug cartridges or for manufacturing non-medical receptacles.

Laser radiation can be used to reshape hollow glass bodies. DE 10 2010 045 094 A1, DE 10 2012 101 948 A1 and DE 10 2016 114 104 A1 describe exemplary methods and systems for laser-assisted reshaping of a glass body.

Laser radiation can also be used to separate hollow glass bodies. DE 10 2011 006 738 A1 describes a method of separating hollow glass, wherein a starting scratch is introduced by means of scratching, the hollow glass is heated by means of laser radiation, subsequently cooled and reheated by means of laser radiation.

Conventional methods of separating a hollow glass body from a glass tube can lead to an undesirably large reduction in the inside diameter at the end of the hollow glass body at which the hollow glass body is separated, for example by scratching and subsequent laser-assisted heating in order to introduce mechanical stresses. Conventional methods of separating a hollow glass body from a glass tube using laser radiation can lead to an undesirably high reject rate during production, which makes the manufacturing method more complex and expensive, and/or can entail a reduced reproducibility.

BRIEF SUMMARY OF THE INVENTION

The problem to be solved by the invention is the provision of improved methods and systems for separating a hollow glass body from a glass tube. In particular, it is desirable to provide such methods and systems which can be used for manufacturing hollow glass bodies which are reshaped into medical or non-medical receptacles. It is desirable to provide such methods and systems which, compared to methods in which a scratch is mechanically introduced into a glass tube and mechanical stresses are subsequently generated by laser-assisted heating in combination with cooling, have an improved reproducibility and a lower reject rate during production. It is desirable to provide such methods and systems by which, compared to methods in which a scratch is mechanically introduced into a glass tube and mechanical stresses are subsequently generated by laser-assisted heating in combination with cooling, a significant reduction in the inside diameter at the end of the hollow glass body can be prevented.

According to the present invention, methods and a system having the features recited in the independent claims are provided. The dependent claims define embodiments.

A method of separating a hollow glass body from a glass tube according to an embodiment comprises laser cutting the glass tube to separate the hollow glass body. A laser beam used for the laser cutting operation may be focused on a wall of the glass tube.

In the method, the hollow glass body can be separated from the glass tube for manufacturing a medical receptacle or a non-medical receptacle.

By focusing the laser beam on a wall of the glass tube, energy densities can be achieved which allow the hollow glass body to be separated even without requiring a scratch to be mechanically introduced. The end of the hollow glass body exposed to the laser beam during separation can have an inside diameter that is only slightly reduced compared to an inside diameter of a cylindrical main portion of the hollow glass body.

The laser beam may be focused so that a focal point of the laser beam is within a wall of the glass tube.

The laser beam may be focused so that on a first side of the glass tube the focal point of the laser beam is within the wall of the glass tube and on an opposite side of the glass tube a laser intensity is no longer sufficient to cut the glass tube. A circumferential laser cut can be generated by a relative movement between the glass tube and the laser beam.

The laser cutting operation may comprise laser sublimation cutting. The laser cutting operation may be carried out in such a way that laser sublimation cutting takes place in a first zone located inside the wall of the glass tube, and in any case melting processes can also take place in a second zone in the wall of the glass tube, said second zone surrounding the first zone.

The laser beam may be a pulsed laser beam which comprises a sequence of pulses having a pulse length and a repetition rate. The method may further include: controlling the pulse length and repetition rate using an open-loop control or using a closed-loop control in order to cut at least a zone of the wall of the glass tube by laser sublimation cutting.

The laser beam may be focused in such a way that a Rayleigh length of the laser beam is equal to or smaller than a wall thickness wt of the glass tube, preferably equal to or smaller than 0.8×wt, preferably equal to or smaller than 0.6×wt, more preferably equal to or smaller than 0.5×wt.

The hollow glass body may be separated from the glass tube without the mechanical introduction of a scratch.

The hollow glass body may be separated from the glass tube at a separation area without any mechanical force being exerted onto the glass tube.

The method may comprise causing a relative rotation between the laser beam and the glass tube during the laser cutting operation.

The relative rotation between the glass tube and the laser beam can be implemented in various ways:
(1) the glass tube is rotated during the laser cutting, and a beam axis of the laser beam is not moved during the laser cutting;
(2) a beam axis of the laser beam is moved, e.g. rotated in a plane perpendicular to the center axis of the glass tube, during the laser cutting and the glass tube is not moved during the laser cutting;
(3) a beam axis of the laser beam is moved, e.g. rotated in a plane perpendicular to the center axis of the glass tube, during the laser cutting and the glass tube is rotated during the laser cutting.

The glass tube may have an outside diameter of less than 30 mm, preferably less than 15 mm, preferably less than 13 mm, more preferably less than 11 mm.

The glass tube may have an inside diameter of less than 28 mm, preferably less than 12 mm, preferably less than 8 mm, more preferably less than 7 mm.

The glass tube may have a wall thickness of less than 1.5 mm, preferably less than 1 mm.

The hollow glass body may be separated from the glass tube in less than 1 s, preferably in less than 0.9 s by means of laser cutting.

The glass tube may consist of glass of hydrolytic class 1 according to DIN 12111 (ISO 719).

The laser radiation may comprise pulses with a repetition rate of 3 kHz to 30 kHz, preferably 4 kHz to 12 kHz.

The laser radiation may be pulsed and may have a pulse-duty factor of between 5% and 35%, preferably between 8% and 17%.

The laser beam may be generated using a $CO_2$ laser.

The laser beam may have a beam diameter at the laser beam focal point which is from 50 to 250 micrometers, preferably from 100 to 200 micrometers.

The glass tube may be rotated during the laser cutting operation at a speed of more than 100 rpm, preferably between 150 rpm and 700 rpm.

The laser beam may be output from a laser nozzle, from which gas exits at a positive pressure. The positive pressure may be greater than 0.1 bar, preferably greater than 0.3 bar.

The glass tube may be accurately aligned on both ends both in an axial direction and in a circumferential direction during the laser cutting operation.

The laser beam may impinge on the wall of the glass tube along a direction transverse to a center axis of the glass tube, in particular perpendicularly to the center axis of the glass tube.

The hollow glass body separated from the glass tube may have a main portion extending along a longitudinal axis of the hollow glass body and having an inside diameter of less than 28 mm, preferably less than 12 mm, preferably less than 8 mm, more preferably less than 7 mm.

The hollow glass body separated from the glass tube may have a main portion extending along a longitudinal axis of the hollow glass body and having an outside diameter of less than 30 mm, preferably less than 15 mm, preferably less than 13 mm, more preferably less than 11 mm.

A method of manufacturing a receptacle according to an embodiment may comprise separating a hollow glass body from a glass tube by means of the method according to an embodiment and optionally reshaping at least a zone of the separated hollow glass body.

The method may be a method of manufacturing a medical receptacle or a non-medical receptacle.

The medical receptacle may be a syringe, a drug cartridge, another medical cartridge, a small bottle or another medical receptacle.

The method may further comprise filling the medical receptacle with a formulation. The formulation may comprise at least one pharmaceutically active substance or a pharmaceutical carrier substance. The pharmaceutical carrier substance may be WFI (water for injection).

The method may further comprise inserting a plug, a syringe plunger, or another closure element into an end of the medical receptacle at which the hollow glass body has been separated from the glass tube by laser cutting.

A system for manufacturing a receptacle comprises a laser unit having a focusing device for focusing a laser beam on a wall of a glass tube for laser cutting the glass tube in order to separate a hollow glass body from the glass tube. The system may comprise a device for causing a relative rotation between the glass tube and the laser beam during the laser cutting operation.

The system may be a system for manufacturing a medical receptacle or a non-medical receptacle.

The system can be configured such that:
(1) for causing a relative rotation, the glass tube is rotated during the laser cutting operation, and a beam axis of the laser beam is not moved during the laser cutting operation;
(2) a beam axis of the laser beam is moved, e.g. rotated in a plane perpendicular to the center axis of the glass tube, during the laser cutting operation and the glass tube is not moved during the laser cutting operation; and
(3) a beam axis of the laser beam is moved, e.g. rotated in a plane perpendicular to the center axis of the glass tube, during the laser cutting operation and the glass tube is rotated during the laser cutting operation.

The system may be configured so that a focal point of the laser beam is within a wall of the glass tube.

The system may be configured so that on a first side of the glass tube the focal point of the laser beam is within the wall of the glass tube and that on an opposite side of the glass tube a laser intensity is no longer sufficient to cut the glass tube. A circumferential cut can be produced by a relative movement between the glass tube and the laser beam.

The system may have a control device for controlling the laser unit. The control device may be configured to control the laser unit such that at least a zone of the wall of the glass tube is cut by laser sublimation cutting. The laser cutting operation can be carried out in such a way that laser sublimation cutting takes place in a first zone located inside the wall of the glass tube, and in any case melting processes can also take place in a second zone in the wall of the glass tube, said second zone surrounding the first zone.

The control device may be configured to control the laser unit to generate a pulsed laser beam which comprises a sequence of pulses having a pulse length and a repetition rate. The control device may be configured to control the pulse length and repetition rate using an open-loop control or using a closed-loop control to cut at least a zone of the wall of the glass tube by laser sublimation cutting.

The focusing device may be configured such that a Rayleigh length of the laser beam is equal to or smaller than a wall thickness wt of the glass tube, preferably equal to or smaller than 0.8×wt, preferably equal to or smaller than 0.6×wt, more preferably equal to or smaller than 0.5×wt.

The laser unit may be configured to generate the laser radiation such that it comprises pulses with a repetition rate of 3 kHz to 30 kHz, preferably 4 kHz to 12 kHz.

The laser unit may be configured to generate the laser radiation such that it has a pulse-duty factor of between 5% and 35%, preferably between 8% and 17%.

The laser unit may comprise a $CO_2$ laser.

The system may be configured such that a beam diameter at the laser beam focal point is from 50 to 250 micrometers, preferably from 100 to 200 micrometers.

The system may be configured to rotate the glass tube during the laser cutting operation at a speed of more than 100 rpm, preferably between 150 rpm and 700 rpm.

The system may comprise a laser nozzle, from which gas exits at a positive pressure. The positive pressure may be greater than 0.1 bar, preferably greater than 0.3 bar.

The system may comprise chucks to accurately align the glass tube on both ends both in an axial direction and in a circumferential direction.

The system may be configured to separate the hollow glass body from the glass tube without the mechanical introduction of a scratch.

The system may be configured to separate the hollow glass body from the glass tube without any mechanical force being exerted at a separation area.

The system may be configured such that the laser beam impinges on the wall of the glass tube along a direction transverse to a center axis of the glass tube, in particular perpendicularly to the center axis of the glass tube.

The system may comprise at least a first drive unit for rotatingly driving the glass tube during the laser cutting operation.

The system may comprise a plurality of devices for holding and rotating a glass tube each. The system may comprise a conveyor device on which the plurality of devices for holding and rotating are arranged.

The system may further comprise a second drive unit for rotatingly driving the conveyor device.

The system may comprise optical components for splitting the laser beam into a plurality of subbeams in order to cut glass tubes held on a plurality of the devices for holding and rotating.

The system may comprise optical components for deflecting the laser beam in order to cut glass tubes held on a plurality of the devices for holding and rotating.

The system may comprise a device for reshaping the hollow glass body separated from the glass tube into a medical receptacle.

The device for reshaping the hollow glass body may be configured to reshape the hollow glass body into a syringe, a drug cartridge, another medical cartridge, a small bottle or another medical receptacle.

The device for reshaping the hollow glass body may be configured to reshape the hollow glass body into a non-medical receptacle.

The system may comprise a device for filling the medical receptacle with a formulation. The device for filling may be configured to fill the medical receptacle with a formulation containing at least one pharmaceutically active substance or a pharmaceutical carrier substance. The pharmaceutical carrier substance may be WFI (water for injection).

The system may further be configured to insert a plug, a syringe plunger, or another closure element into an end of the medical receptacle at which the hollow glass body has been separated from the glass tube by laser cutting.

The system may be configured to perform the method according to an embodiment.

Methods and systems according to the present invention can be used for manufacturing hollow glass bodies which are reshaped into medical receptacles. Compared to methods in which a scratch is mechanically introduced into a glass tube and mechanical stresses are subsequently generated by laser-assisted heating in combination with cooling, an improved reproducibility is achieved and the reject rate during production is reduced. An undesirably large reduction in the inside diameter of the hollow glass body at the end separated by laser cutting can be prevented.

BRIEF DESCRIPTION OF DRAWINGS

Exemplary embodiments of the invention are described in detail with reference to the Figures, in which similar or identical reference signs designate similar or identical elements.

FIG. 4 shows a beam profile of a laser beam used for laser cutting in a method and system according to an embodiment.

FIG. 5 shows a time-dependent output power of a laser beam used for laser cutting in a method and system according to an embodiment.

DETAILED DESCRIPTION OF EMBODIMENTS

Methods and systems for separating hollow glass bodies from a glass tube for manufacturing a receptacle are described in the following with reference to the Figures. Although some exemplary embodiments are described in the context of specific medical receptacles such as syringes or drug cartridges or in the context of specific laser arrangements, the embodiments are not limited thereto. The methods and systems according to the invention can also be used for manufacturing non-medical receptacles or other objects.

Methods and systems according to embodiments enable a hollow glass body to be separated from a glass tube by means of laser radiation. The separation can be performed such that no mechanical force must be exerted at a separation area of the glass tube for separating the hollow glass body. The separation can be achieved in that laser sublimation cutting is performed in at least a zone of a wall of the glass tube. In an adjacent zone, the glass can optionally be melted, in addition to or instead of sublimation.

The methods and systems may comprise an optional further treatment of the separated hollow glass body. For example, the separated hollow glass body can be reshaped into a syringe, drug cartridge or other medical cartridge. The hollow glass body can be reshaped into a non-medical receptacle.

Figure 1:
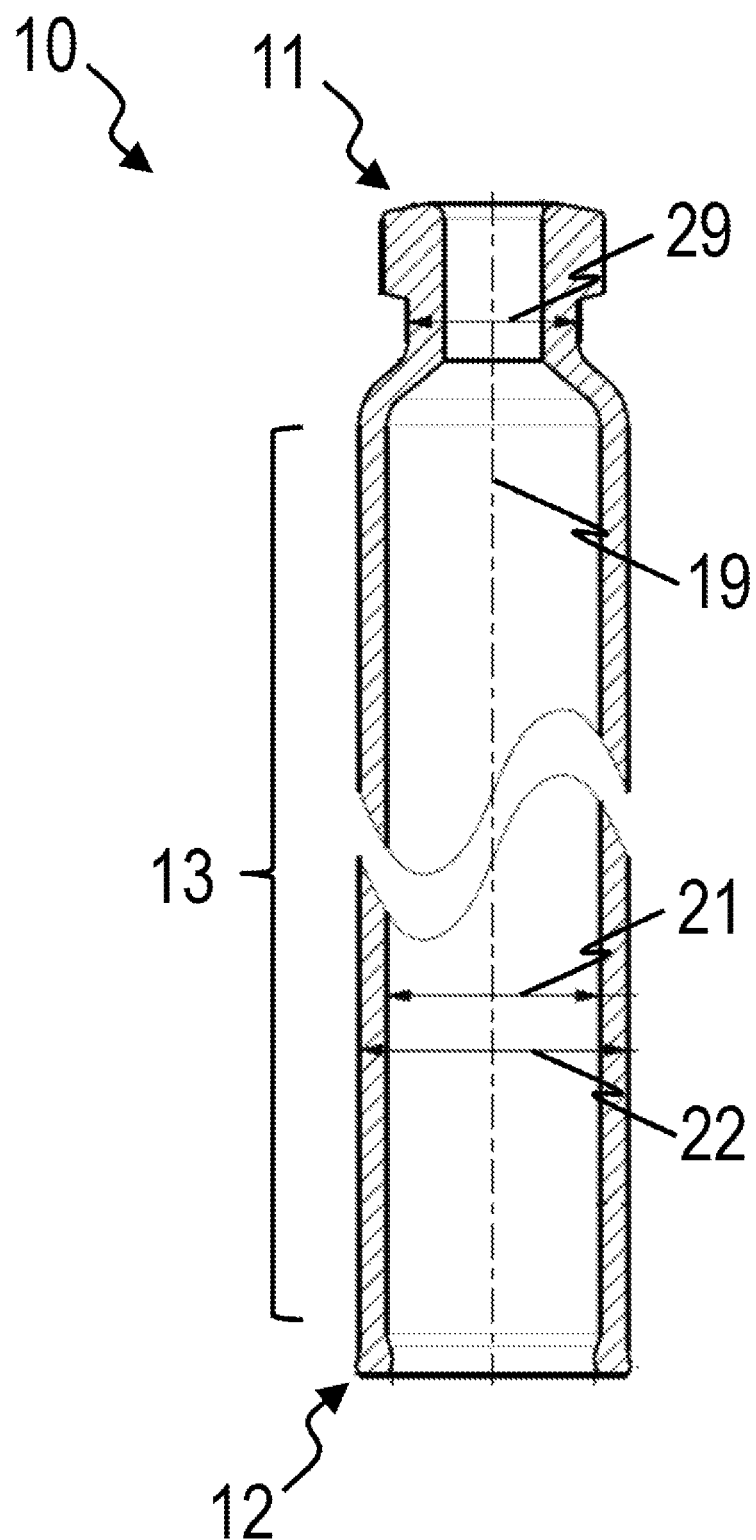
FIG. 1 is a sectional view of a medical receptacle produced with the method and system according to an embodiment.
Figure 2:
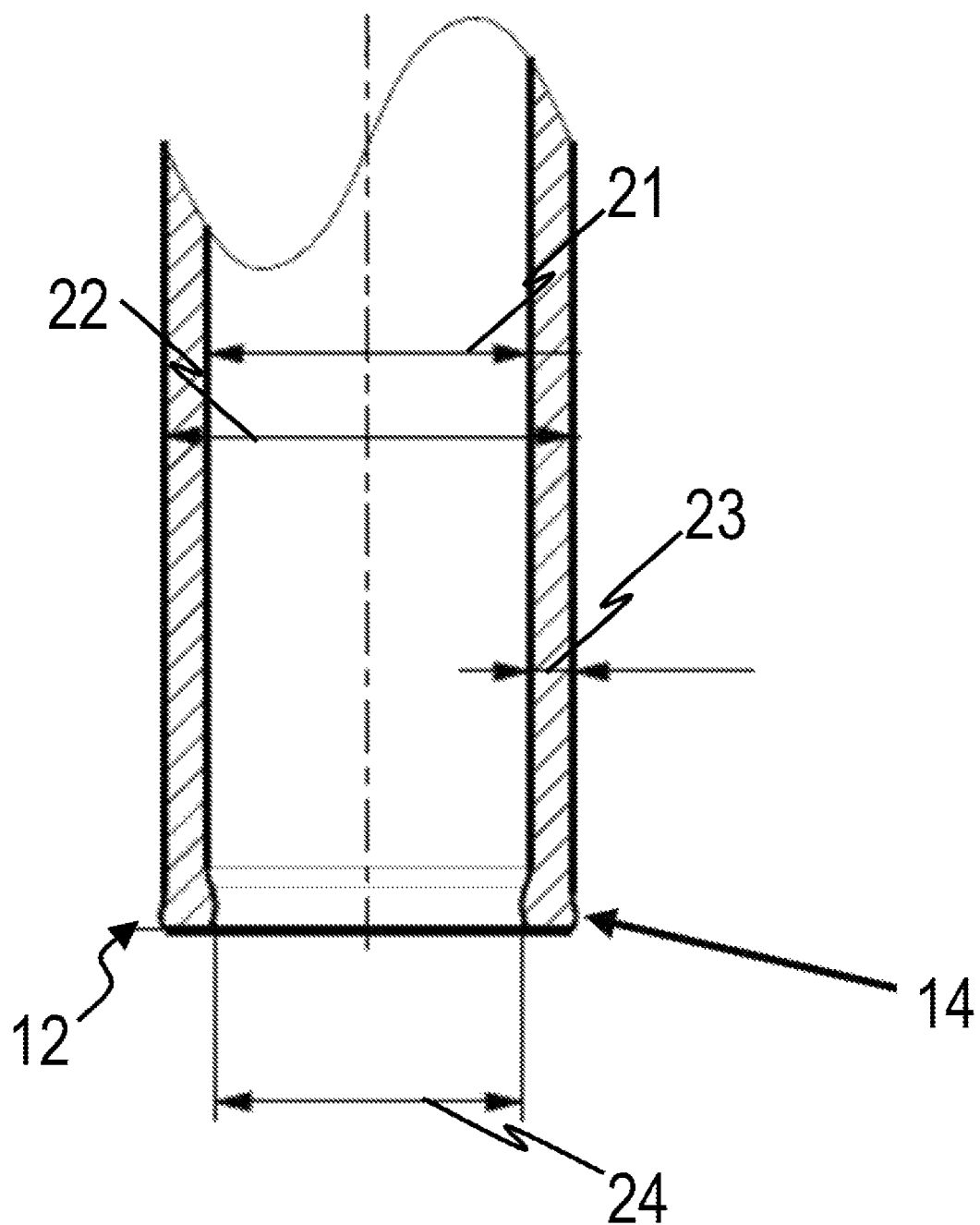
FIG. 2 is a detail view of the medical receptacle of FIG. 1.

FIG. 1 is a sectional view of a receptacle 10 manufactured with the method and system according to an embodiment. FIG. 2 is a detail view of the receptacle 10 of FIG. 1. The receptacle 10 may be a medical receptacle or a non-medical receptacle.

The receptacle 10 may be made of a hollow glass body. The receptacle 10 may consist of glass of hydrolytic class 1 according to DIN 12111 (ISO 719) or comprise such glass.

The receptacle 10 has a first end 12, at which the hollow glass body has been separated from a glass tube by laser cutting. The receptacle 10 has a second end 11 spaced apart from the first end 12. For example, the second end 11 can be formed into a collar shape in which an outside diameter of the receptacle 10 has a constriction 29.

The receptacle 10 has a cylindrical main portion 13 arranged between the first end 12 and the second end 11. The receptacle 10 can extend rotationally symmetrically about a centre-center axis 19 at least in the cylindrical main portion 13 and advantageously along its entire length.

In its cylindrical main portion 13, the receptacle can have an inside diameter 21, an outside diameter 22 and a wall thickness 23. The outside diameter 22 can be less than 30 mm, preferably less than 15 mm, preferably less than 13 mm, more preferably less than 11 mm. The inside diameter 21 can be less than 28 mm, preferably less than 12 mm, preferably less than 8 mm, more preferably less than 7 mm. The wall thickness 23 can be less than 1.5 mm, preferably less than 1 mm.

The first end 12 of the receptacle may have a shape defined by the laser cutting operation during the separation of the hollow glass body. In particular, the receptacle 10 can be shaped from the hollow glass body separated from the glass tube in such a way that only the second end 11, but not the first end 12, is further reshaped after the hollow glass body has been separated from the glass tube. Thus, the first end 12 of the receptacle may have a laser cut 14 which is generated when the hollow glass body is separated from the glass tube and which is not subsequently reshaped again.

Due to the separating operation, the first end 12 may have an inside diameter 24. The inside diameter 24 may be the clear width of the first end 12. The methods and systems according to the present invention allow a difference A between the inside diameter 24 at the first end 12 and the inside diameter 21 of the cylindrical portion 13 to be reduced compared to conventional methods, which, in addition to the use of laser radiation, also require the introduction of a starting scratch to separate the hollow glass body from the glass tube. Due to the methods and systems according to the present invention, the reduction of the inside diameter at the end 12 can thus be kept smaller than with conventional methods and systems.

For example, the difference A can be smaller than 0.1 mm, preferably smaller than 0.05 mm. Such a small reduction of the clear width at the end 12 of the receptacle 10 which has been separated by laser radiation entails numerous advantages, for example in the further mechanical handling of the medical receptacle 10 for filling and/or closing the receptacle 10.

With reference to FIGS. 3 to 10, methods and systems are described in detail which allow a hollow glass body to be separated from a glass tube, wherein the hollow glass body may subsequently be reshaped into the medical or non-medical receptacle 10.

Figure 3:
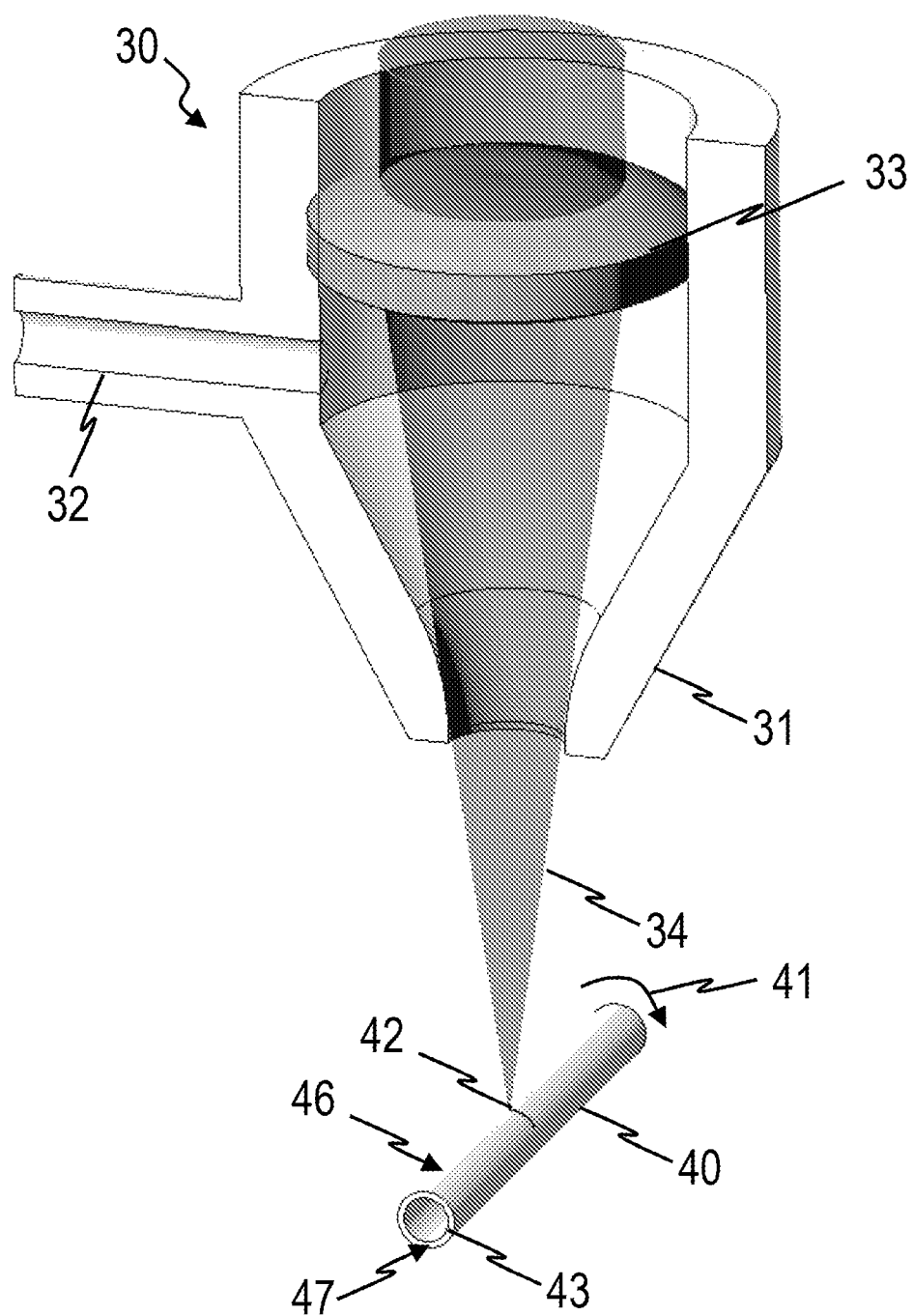
FIG. 3 is a schematic illustration of a laser cutting operation to separate a hollow glass body from a glass tube in a method and system according to an embodiment.

FIG. 3 shows components of a system 30 for separating a hollow glass body from a glass tube 40 by laser cutting. The separation can be carried out without the exertion of mechanical force at a separation area, in particular without the introduction of a starting scratch at the separation area of the glass tube 40. The laser cutting operation can comprise laser sublimation cutting in at least a zone of the glass tube 40.

The glass tube 40 may consist of glass of hydrolytic class 1 according to DIN 12111 (ISO 719). The glass tube 40 may consist of borosilicate glass.

A laser beam 34 is focused on a wall of the glass tube 40 by a lens 33 in a laser nozzle 31. While only one lens 33 is shown in FIG. 3, a lens system that can comprise a plurality of lenses may be used to focus the laser beam 34.

The laser nozzle 31 may comprise a gas passage 32. Pressurized gas can leave the laser nozzle 31 along the same opening as the laser beam 34 collimated by the lens 33. Fumes generated during laser cutting, for example, can be removed by the pressurized gas. The side of the focusing device facing the glass tube during laser cutting, such as a side of the front lens 33 facing the glass tube during laser cutting, can be protected.

The glass tube 40 comprises a wall 43. The wall 43 may extend cylindrically around a center axis of the glass tube 40. The glass tube 40 may be rotated around its center axis during the laser cutting operation in order to produce a circumferential laser cut 42. A rotational axis of the rotation 41 of the glass tube 40 may be perpendicular to a center axis of the laser beam 34.

The laser beam 34 can be focused on the glass tube 40 by the focusing device 33 in such a way that a focal point of the laser beam 34 is arranged on a surface or within a wall thickness on the side 46 of the glass tube 40 facing the focusing device 33. The wall on the opposite side 47 of the glass tube 40 may be spaced apart from the focal point of the laser beam 34. By a rotation 41 of the glass tube 40, the wall 43 can be gradually displaced across the focal point of the laser beam along the circumference of the glass tube 40 to generate a circumferential cut.

For a good laser cutting operation, in particular for a laser cutting operation comprising laser sublimation cutting in at least a zone of the wall 43, a beam profile of the laser beam 34 focused by the focusing device 33 may be adjusted to a wall thickness of the glass tube 40. The adjustment of the beam profile to the wall thickness of the glass tube 40 can be achieved by a suitable selection and/or positioning and/or setting of the focusing device 33.

FIG. 4 shows a beam profile of the laser beam 34 focused by the focusing device 33 and a wall thickness 44 of the wall 43 of the glass tube 40 from which the hollow glass body is separated.

The beam profile is adjusted to the wall thickness 44 such that a Rayleigh length 38 is equal to or smaller than the wall thickness 44 (which is referred to in the following as wt). The Rayleigh length 38 may advantageously be equal to or smaller than 0.8× wt, in particular equal to or smaller than 0.6×wt, in particular equal to or smaller than 0.5×wt.

The Rayleigh length 38 can be defined as distance along the beam axis 35 between a beam waist, at which the laser beam has a minimum beam diameter along a beam axis 35, and a position at which a radius 37 of the laser beam 43 is $\sqrt{2}$ times the radius 36 at the beam waist.

For a good laser cutting operation, in particular for a laser cutting operation comprising laser sublimation cutting in at least a zone of the wall 43, a laser source of the laser beam 34 can generate a pulsed laser beam. A repetition rate and/or a pulse-duty factor of the pulsed laser beam may be set so that laser sublimation cutting takes place in at least a zone of the wall 43.

FIG. 5 shows a pulse train 50 of intensity pulses which are generated by a laser source and can be used to separate the hollow glass body from the glass tube 40 by laser cutting. The pulse train 50 comprises a plurality of pulses each having a length 51. Consecutive pulses are separated by an interval 53 without the emission of laser light. A time interval 52 between consecutive rising edges of consecutive pulses of the pulse train 50 is the inverse of the repetition rate. The pulse-duty factor is defined as the duration 51 of a pulse divided by the time interval 52 that occurs between consecutive rising pulse edges and that defines the inverse of the repetition rate.

The following steps can be performed to determine suitable parameters for the repetition rate, the pulse-duty factor and optionally further parameters such as the laser frequency and/or laser power:

(a) Firstly, a parameter field may be defined which is spanned by a plurality of parameters. The plurality of parameters may comprise the repetition rate, the pulse-duty factor and the laser power. In an exemplary embodiment, the parameter field can be defined by repetition rates of 1 kHz to 200 kHz, a pulse-duty factor of 7% to 50% and a laser power of 0.2 kW to 1 kW.

(b) The parameter field can be tested by selecting points of the parameter field with a step size along the different parameter axes.

(c) Laser cutting is performed with the respective parameters.

(d) The laser cut is evaluated by quantitative quality criteria such as the change A of the inside diameter at the end of the hollow glass body treated with laser cutting and/or the roundness of the cut edges.

(e) Steps (b) to (d) are repeated with smaller step sizes around the regions of the parameter field which have been identified as particularly suitable in the previous iteration.

In exemplary embodiments, the laser source can be controlled so that a pulse train with a repetition rate of 3 kHz to 30 kHz, preferably of 4 kHz to 12 kHz, and a pulse-duty factor of between 5% and 35%, preferably between 8% and 17%, is generated and used for laser cutting.

In advantageous embodiments, the laser cutting operation comprises laser sublimation cutting. Laser sublimation cutting does not have to extend across the entire wall thickness but can be combined with other laser cutting processes that may include melting.

Figure 6:
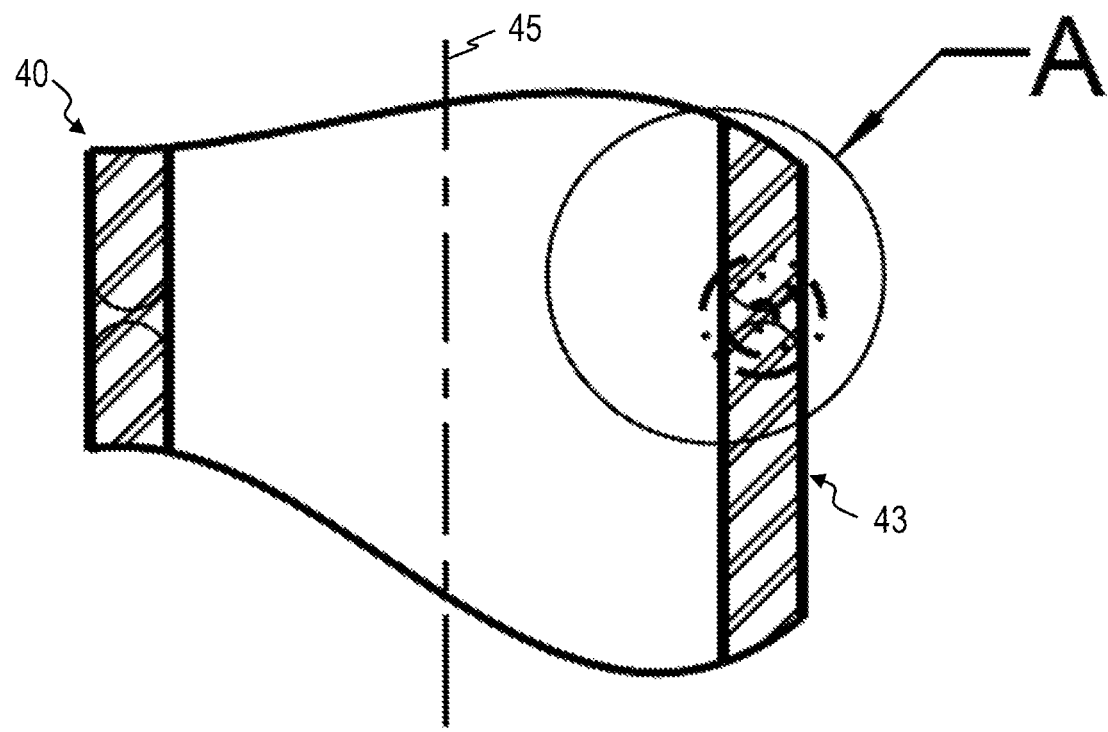
FIG. 6 is a sectional view of a glass tube during the laser cutting operation in a method and system according to an embodiment.
Figure 7:
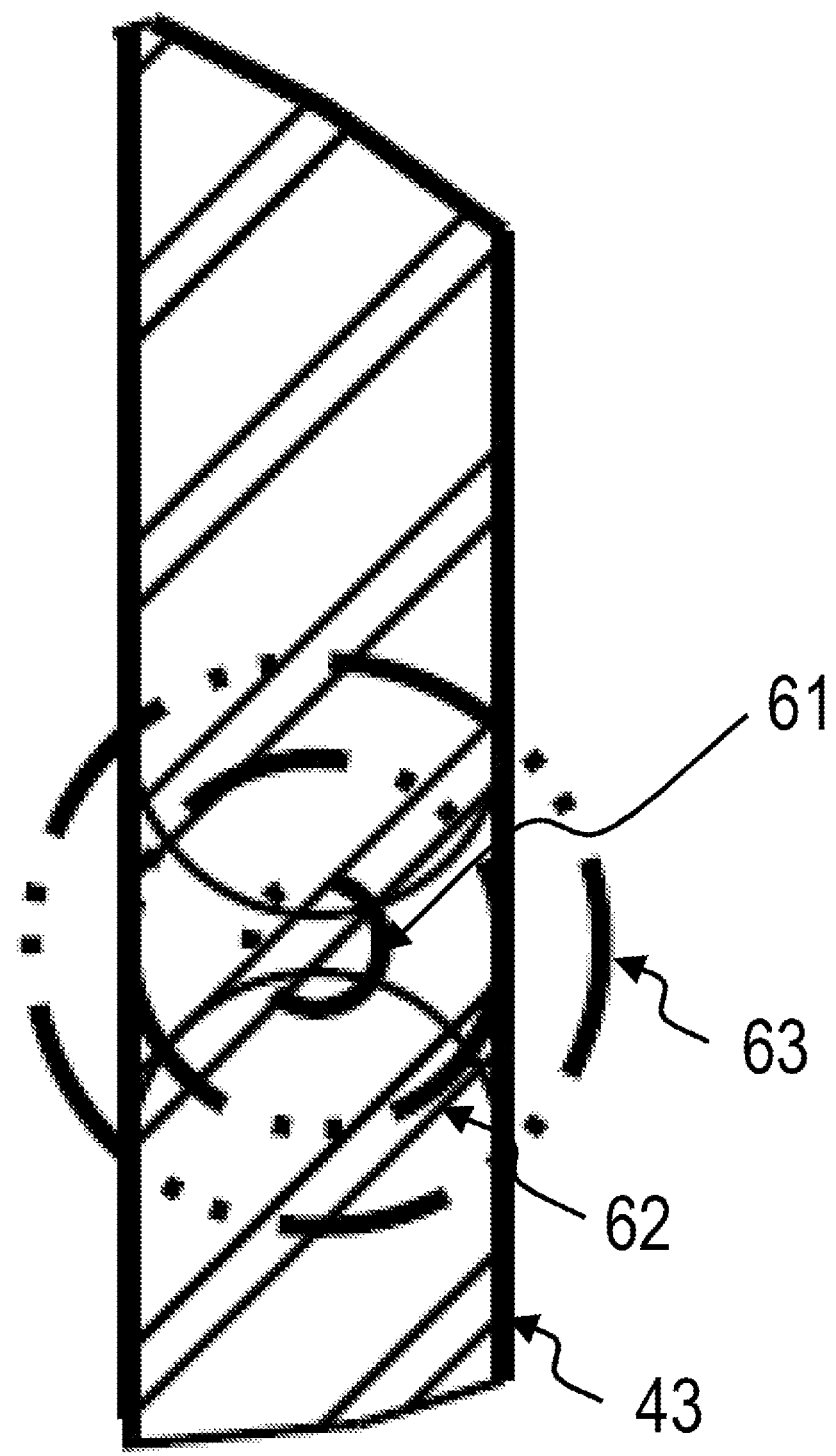
FIG. 7 is an enlarged view of detail A of FIG. 6.

FIG. 6 shows a sectional view of a glass tube 40 to be cut with laser radiation. FIG. 7 shows an enlarged view of the detail A marked in FIG. 6.

During laser cutting, the laser beam can be focused on the wall 43 so that the laser beam has a sublimation zone 61 in the center which is aligned concentrically to the beam profile. In the sublimation zone 61, separation by sublimation takes place. In a mixed zone 62 surrounding the sublimation zone 61, the glass of the glass tube 40 is sublimated and melted. The mixed zone 62 is surrounded by a melting zone 63 which generates a radius on the inner and outer surfaces of the wall 43 both on the separated hollow glass body and on the remaining rest of the glass tube, said radius being most clearly visible in FIG. 7. In every sectional plane that includes the center axis of the glass tube 40, the radius forms an arch extending from the inner side to the outer side of the glass tube 40. A tangent of the arch can transition tangentially or approximately tangentially into the inner side and the outer side of the glass cylinder.

The methods and systems according to embodiments may be configured in such a way that the hollow glass body is separated from the glass tube 40 in less than 1 s, preferably in less than 0.9 s by means of laser cutting.

The methods and systems according to embodiments may be integrated into industrial manufacturing methods in a suitable manner so that a plurality of glass tubes can be efficiently treated.

Figure 8:
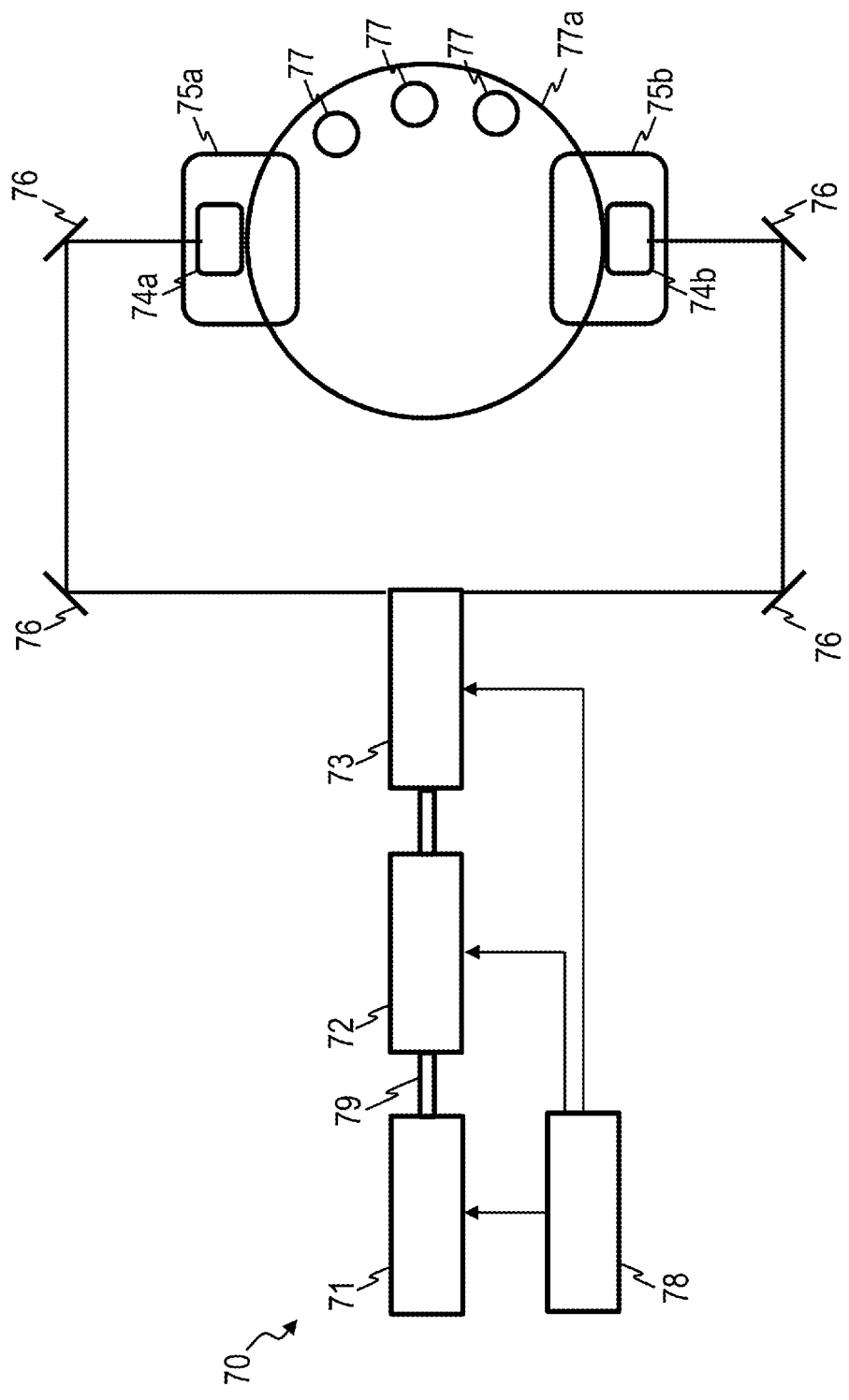
FIG. 8 is a schematic illustration of a system according to an embodiment.

FIG. 8 is a schematic illustration of a system 70 for manufacturing a medical or non-medical receptacle. The system 70 may be configured to separate a hollow glass body from a glass tube by laser cutting. The system 70 may optionally be configured to further reshape the hollow glass body separated from the glass tube and/or to fill and/or close the reshaped hollow glass body.

The system 70 comprises a laser source 71 and a control device 78. The laser source 71 may be configured to emit a pulsed laser beam. The control device 78 may be configured to control a repetition rate and/or pulse-duty factor of the pulse train using an open-loop control or using a closed-loop control, as described above.

The system 70 may optionally comprise a laser polarizer 72 and/or a laser switch 73. The control device 78 can be configured to control the laser polarizer 72 and/or the laser switch 73 using an open-loop control or using a closed-loop control, for example in order to selectively provide a laser radiation 79 to one of a plurality of laser heads 74a, 74b.

The system 70 can comprise a plurality of devices 77, each of which is configured to hold and optionally to rotate a glass tube and only some of which are illustrated in FIG. 8. The devices 77 can rotate the glass tubes they are holding while one of the laser heads 74a, 74b performs a laser cutting operation.

The plurality of devices 77 for holding and optionally for rotating a glass tube can be arranged on a conveyor device 77a. The devices 77 may each be rotatably mounted on the conveyor device 77a. The system 70 may comprise a drive device for rotatingly driving the devices 77. The devices 77 may be arranged so as to be spaced apart from each other along a circumference of the conveyor device 77a.

The conveyor device 77a may itself be rotatably mounted. The system 70 may comprise a further drive device for rotatingly driving the conveyor device 77a. The drive devices can be controlled by the control device 78 or a separate control device. The drives of the conveyor device 77a and of the devices 77 can be activatable independently of each other.

The laser beam generated by the laser source 71 can be directed to one or more laser heads 74a, 74b via optical components 76, for example mirrors. Each of the laser heads 74a, 74b may have a focusing device as described with reference to FIGS. 3 to 7. Each of the laser heads 74a, 74b may comprise a laser nozzle 31 as described with reference to FIG. 3.

A plurality of laser heads 74a, 74b may be arranged at different positions along the circumference of the conveyor device 77a. The laser heads 74a, 74b may be stationarily mounted in the system 70, but may also comprise mechanically movable components, for example for laser beam tracking. The laser heads 74a, 74b and/or the devices 77 may be configured such that the laser beam emitted by a laser head 74a, 74b for laser cutting is mechanically made to track or follow a respective device 77 each time the respective device 77 moves past the laser head 74a, 74b.

The laser heads 74a, 74b may be respectively mounted in safety housings 75a, 75b.

The system 70 may be configured to manufacture a drug cartridge or another medical cartridge. Further processing stations may be arranged along the circumference of the conveyor device 77a. For example, a processing station for reshaping the hollow glass body after the hollow glass body has been separated from the glass tube may be provided. A processing station for filling and/or closing the reshaped hollow glass body may be provided.

While FIG. 8 schematically illustrates two laser heads 74a, 74b along the circumference of the conveyor device 77a, it is also possible that only one laser head is provided. It is also possible that more than two laser heads are positioned along the circumference of the conveyor device 77a.

The system 70 may be an index machine in which the conveyor device 77a is repeatedly stopped for laser cutting. The laser heads 74a, 74b may be mounted in a stationary manner.

The system 70 may also be configured such that laser beam tracking is performed during laser cutting while a glass tube is continuously moved past a laser head. Such a configuration will be described in more detail with reference to FIG. 10.

Figure 9:
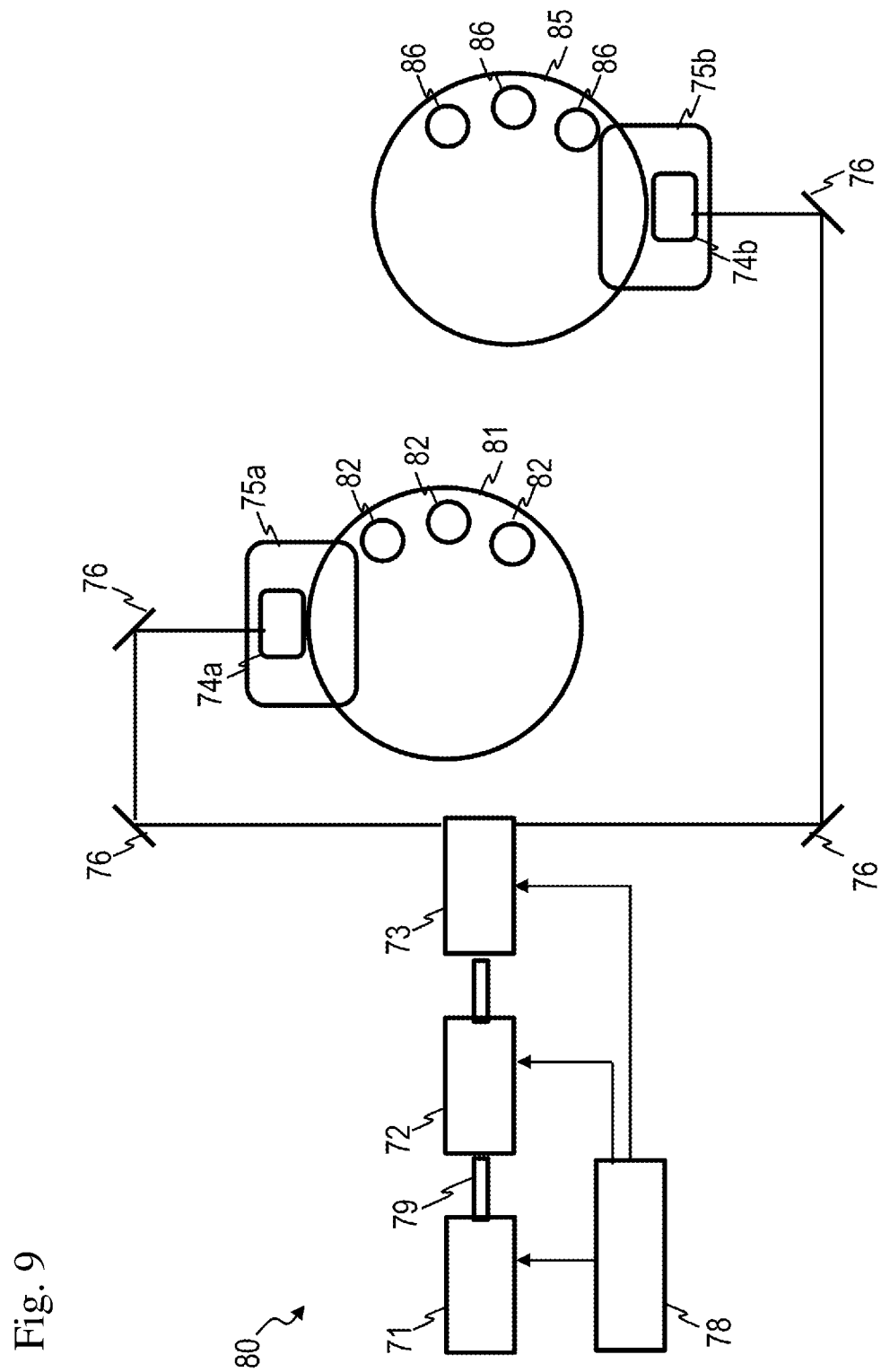
FIG. 9 is a schematic illustration of a system according to an embodiment.

FIG. 9 is a schematic illustration of a system 80 for manufacturing a medical or non-medical receptacle. The system 80 may be configured to separate a hollow glass body from a glass tube by laser cutting. The system 80 may optionally be configured to further reshape the hollow glass body separated from the glass tube and/or to fill and/or to close the reshaped hollow glass body.

The system 80 comprises a laser source 71 and a control device 78, which can be configured and designed as described with reference to FIG. 8. A laser polarizer 72, a laser switch 73 and optical components 76 may also be configured as described with reference to FIG. 8.

The system 80 comprises a conveyor device 81 having a plurality of devices 82 positioned thereon for holding and optionally rotating a glass tube. The conveyor device 81 may be rotatingly drivable. Each of the devices 82 may be rotatingly drivable relative to the conveyor device 81. The devices 82 may rotate the glass tube held by them, while a laser head 74a performs a laser cutting operation. The laser head 74a and/or the devices 82 may be configured such that the laser beam emitted by the laser head 74a for laser cutting is mechanically made to track or follow a respective device 82 each time the respective device 82 moves past the laser head 74a.

The system 80 comprises a further conveyor device 85 having a plurality of further devices 86 positioned thereon for holding and optionally rotating a glass tube. The further conveyor device 85 may be rotatingly drivable. Each of the further devices 86 may be rotatingly drivable relative to the conveyor device 85. The further devices 86 may rotate the glass tube held by them, while a further laser head 74b performs a laser cutting operation. The further laser head 74b and/or the further devices 86 may be configured such that the laser beam emitted by the further laser head 74b for laser cutting is mechanically made to track or follow a respective further device 86 each time the respective further device 86 moves past the further laser head 74b.

The conveyor device 81 and/or the further conveyor device 85 may each form devices for manufacturing syringes. The system 80 may comprise further stations, which may be positioned on the conveyor device 81 and/or on the further conveyor device 85 to reshape the hollow glass body after the hollow glass body has been separated from the glass tube, to fill the reshaped hollow glass body and/or to close the reshaped hollow glass body.

The system 80 may be an index machine in which the conveyor devices 81, 85 are repeatedly stopped for laser cutting. The laser heads 74a, 74b may be mounted in a stationary manner.

The system 80 may also be configured such that laser beam tracking is performed during laser cutting while a glass tube is continuously moved past a laser head. Such a configuration will be described in more detail with reference to FIG. 10.

Figure 10:
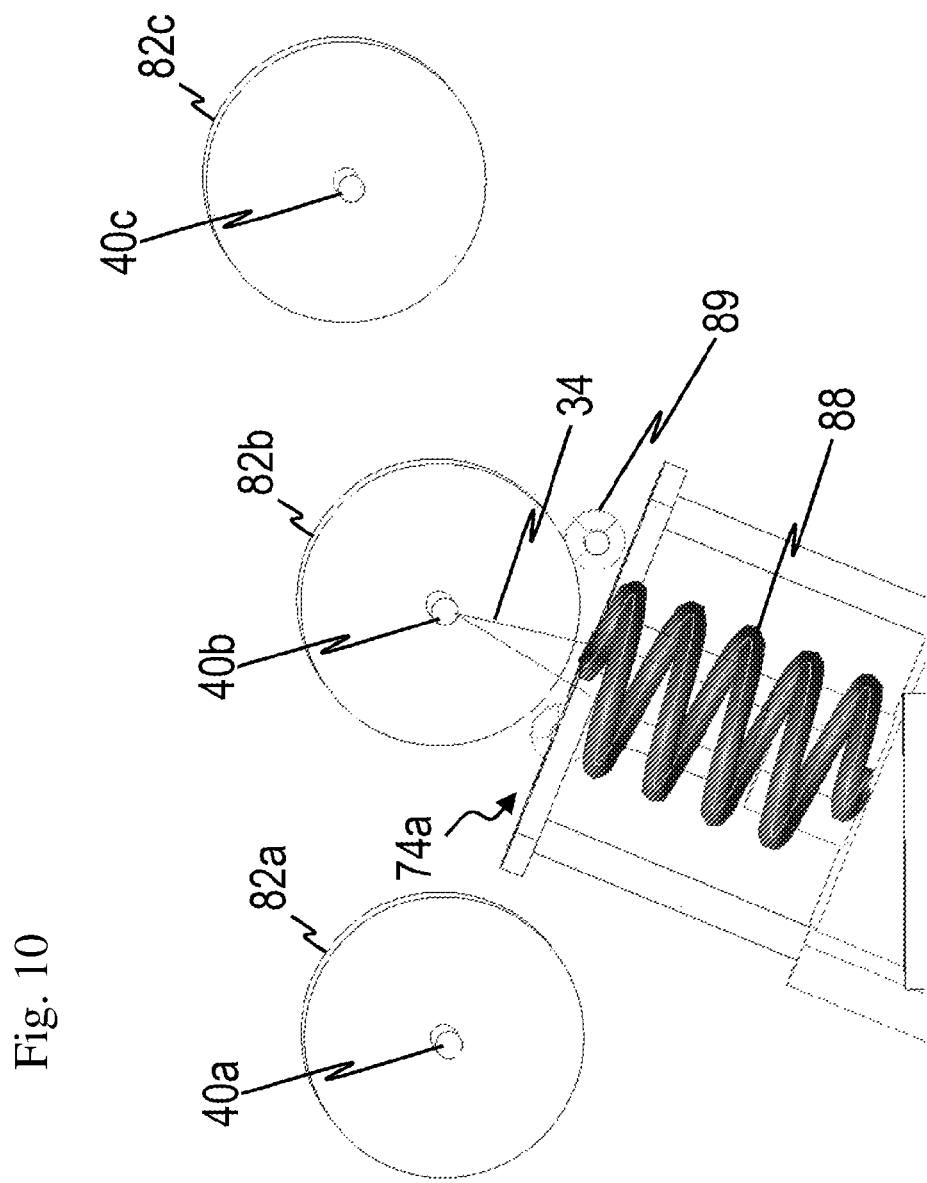
FIG. 10 is an enlarged partial view of components of the systems of FIG. 8 and FIG. 9.

FIG. 10 is an enlarged perspective view of components of the systems 70, 80. The systems 70, 80 comprise a plurality of rotatably mounted devices 82a, 82b, 82c, which can each be arranged on a conveyor device which can be driven independently of the rotatably mounted devices 82a, 82b, 82c. Each of the devices 82a, 82b, 82c may be configured to hold and rotate a glass tube 40a, 40b, 40c.

A laser head 74a may be mounted such that a laser beam 34 is mechanically made to track a respective device 82a, 82b, 82c when the respective device 82a, 82b, 82c is guided past the laser head 74a. The laser head 74a may be biased by a spring-elastic element 88 towards the devices 82a, 82b, 82c. Rollers 89, a rocker or other tracking members can be provided to mechanically move the laser head when one of the devices 82a, 82b, 82c is moved past the laser head 74a.

Various disadvantages associated with conventional methods and systems can be eliminated or mitigated with the methods and systems according to exemplary embodiments. For example, hollow glass bodies and medical or non-medical receptacles can be manufactured whose inside diameter at the end treated with laser radiation is only slightly reduced compared to the inside diameter in a cylindrical main portion.

Figure 11:
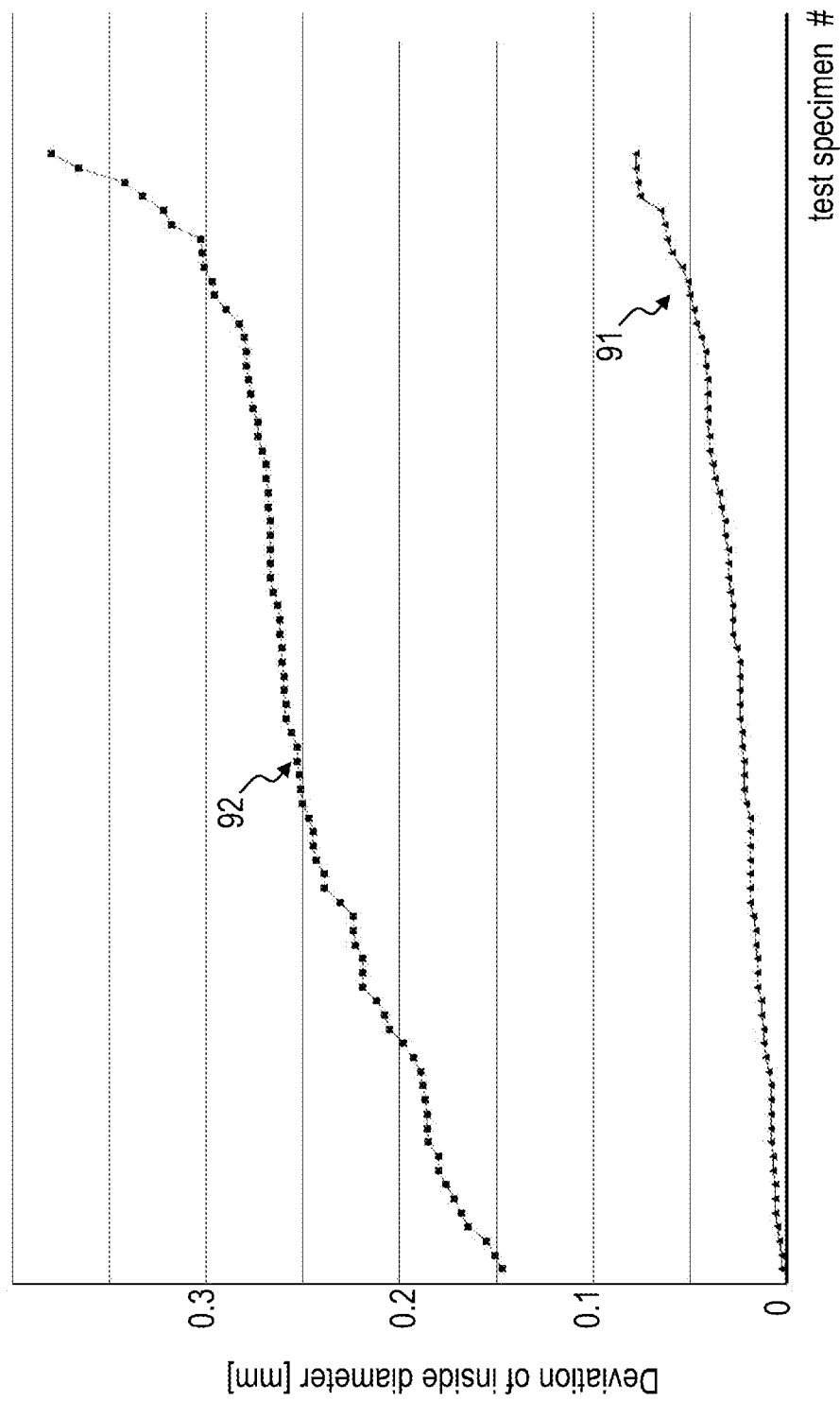
FIG. 11 shows a reduction in inside diameters at the end of a separated hollow glass body for test specimens separated by methods according to the present invention and for test specimens separated by conventional methods.

FIG. 11 shows data of inside diameter deviations $\Delta$ measured in a large number of test specimens. The inside diameter deviation $\Delta$ can be defined as the difference between the inside diameter at an end of the hollow glass body treated with laser cutting and the inside diameter of the cylindrical main portion of the hollow glass body, as described with reference to FIG. 2 for the medical receptacle. In FIG. 11, the inside diameter deviations are plotted as a function of a number of the measured test specimen.

The first data 91 were measured in hollow glass bodies which have been separated from a glass tube by means of methods and systems according to the present invention. The second data 92 were measured in hollow glass bodies which were separated from an identical glass tube by means of conventional methods and systems, wherein in the conventional methods and systems a starting scratch was mechanically introduced and the glass tube was subsequently heated by means of laser radiation and cooled again.

Both the first data 91 and the second data 92 were determined for hollow glass bodies each having a first inside diameter of 6.85±0.15 mm and an outside diameter in the cylindrical main portion of 8.65±0.15 mm. The wall thickness wt of the glass tube from which the hollow glass body was separated and of the main portion of the separated hollow glass body was 0.9±0.1 mm. The glass tube from which the hollow glass body was separated and the hollow glass body each consist of glass of hydrolytic class 1.

Both the first data 91 and the second data 92 were obtained when using a $CO_2$ laser having a wavelength of 10.6 micrometers.

The measured inside diameter deviations for the test specimens were sorted in an in-creasing sequence of inside diameter deviation, both for the hollow glass bodies produced with a method according to the invention and the conventional hollow glass bodies. The test specimens were subsequently numbered in a consecutive manner. Thus, the data 91 and the data 92 show a monotonous increase of the inside diameter deviations which reflects the fact that the test specimens have been sorted and numbered according to the inside diameter deviations. What is essential is that the hollow glass bodies produced with a method according to the invention have inside diameter deviations 91 that are significantly smaller than the inside diameter deviations 92 of the conventional test specimen.

As can be deduced from FIG. 11, the hollow glass bodies manufactured with methods and systems according to the present invention have an inside diameter deviation at the end treated with laser radiation which is significantly smaller than in the hollow glass bodies manufactured with conventional methods and systems. In particular, an inside diameter deviation of less than 0.1 mm, and on average even less than 0.05 mm, can be attained in the hollow glass bodies manufactured with the methods and systems according to the present invention.

For the hollow glass bodies as represented by the first data 91, the inside diameter deviation divided by the first inside diameter is less than 0.016, on average even less than 0.008.

For the hollow glass bodies as represented by the first data 91, the inside diameter deviation divided by the wall thickness in the cylindrical main portion is less than 0.12, on average even less than 0.06.

Methods and devices according to exemplary embodiments can be used for manufacturing hollow glass bodies wherein
  the inside diameter deviation $\Delta$ is at most 100 μm, and/or
  the inside diameter deviation $\Delta$ divided by the inside diameter of the cylindrical main body is smaller than 0.02, preferably smaller than 0.01, preferably smaller than 0.007, more preferably smaller than 0.005, and/or
  the inside diameter deviation $\Delta$ divided by the wall thickness is smaller than 0.2, preferably smaller than 0.1, preferably smaller than 0.07, more preferably smaller than 0.05,
  without the methods and devices being limited thereto.

Figure 12:
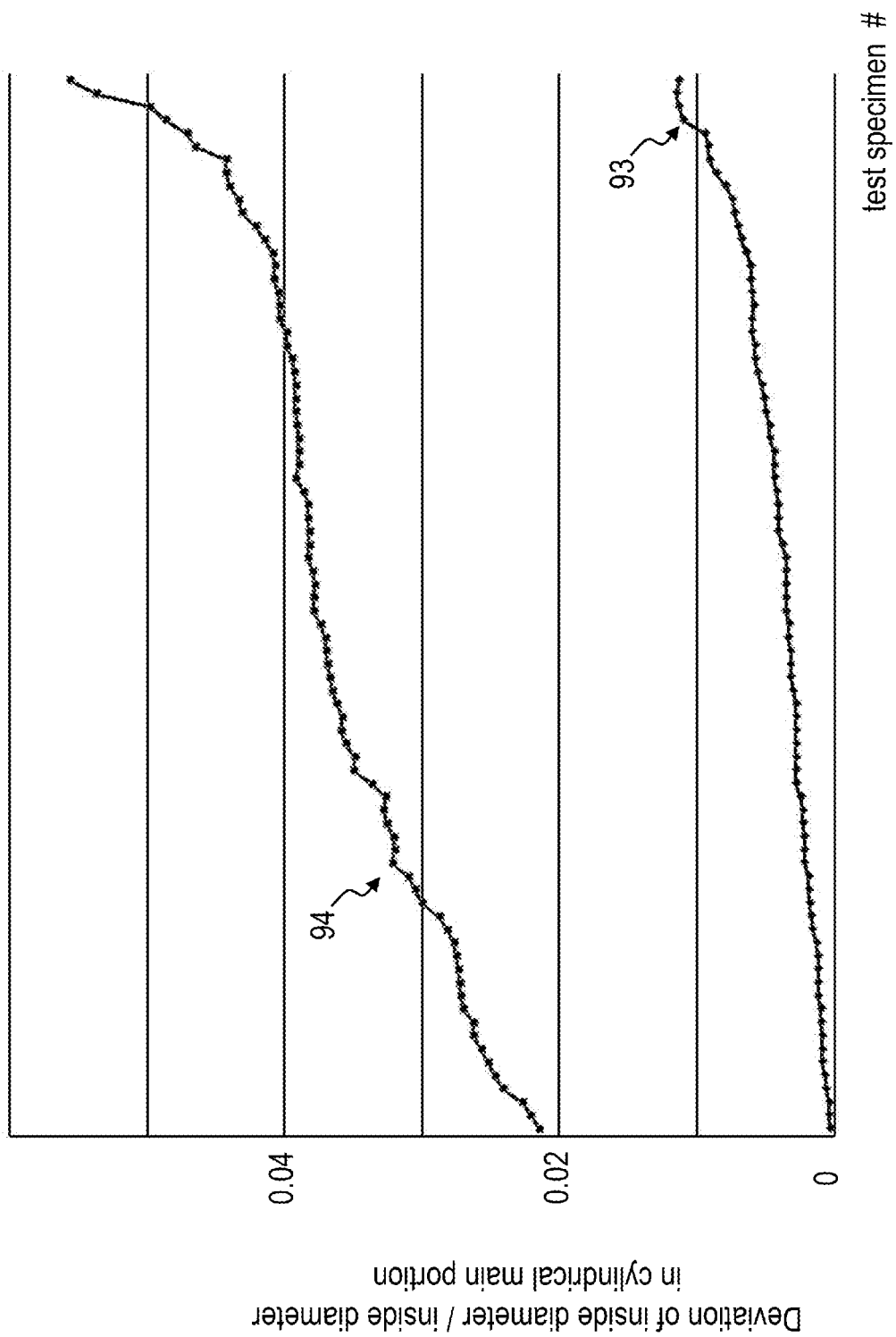
FIG. 12 shows a ratio of the reduction in inside diameter at the end of a separated hollow glass body and an inside diameter of a cylindrical main portion of the hollow glass body, wherein data are shown both for test specimens separated by a method according to the present invention and for test specimens separated by a conventional method.

FIG. 12 shows, in an exemplary manner, the inside diameter deviation $\Delta$ divided by the inside diameter of the cylindrical main body of the respective hollow glass body for the hollow glass bodies for which the inside diameter deviation is shown in FIG. 11. The data 93 represent the ratio of the inside diameter deviation $\Delta$ and the inside diameter of the cylindrical main body for the test specimens produced by the method according to the present invention. The data 94 represent the ratio of the inside diameter deviation $\Delta$ and the inside diameter of the cylindrical main body for the test specimens produced by the conventional method described above. The test specimens produced by the method according to the present invention have a ratio 93 of the inside diameter deviation $\Delta$ and the inside diameter of the cylindrical main body that is less than 0.02. The ratio of the inside diameter deviation $\Delta$ and the inside diameter of the cylindrical main body can be significantly reduced by the method according to the present invention.

Similarly, a ratio of the inside diameter deviation $\Delta$ and the wall thickness of the cylindrical main portion of the hollow glass body can be significantly reduced by the method according to the present invention.

Methods and devices according to exemplary embodiments can be used for manufacturing syringes or drug cartridges, without being limited thereto.

The invention claimed is:

1. A method for separating a hollow glass body from a glass tube, the method comprising:
  laser cutting the glass tube to separate the hollow glass body, wherein:
  a laser beam used for the laser cutting is focused on a wall of the glass tube;
  and
  radiation of the laser beam comprises pulses with a repetition rate of 3 kHz to 30 kHz and
  a pulse-duty factor of between 5% and 35%.

2. The method according to claim 1,
wherein the laser cutting comprises laser sublimation cutting.

3. The method according to claim 2, further comprising:
controlling a pulse length and a repetition rate using an open-loop control or a closed-loop control to cut at least a zone of the wall of the glass tube by the laser sublimation cutting.

4. The method according to claim 1,
wherein the laser beam is focused such that a Rayleigh length of the laser beam is equal to or smaller than a wall thickness of the glass tube.

5. The method according to claim 1,
wherein the hollow glass body is separated from the glass tube without a mechanical introduction of a scratch.

6. The method according to claim 1, further comprising:
causing a relative rotation between the laser beam and the glass tube during the laser cutting.

7. The method according to claim 1,
wherein the glass tube has an outside diameter of less than 30 mm or an inside diameter of less than 28 mm.

8. The method according to claim 7,
wherein the hollow glass body is separated from the glass tube in less than 1 s by the laser cutting.

9. A method of manufacturing a receptacle, the method comprising:
separating a hollow glass body from a glass tube by the method according to claim 1; and
reshaping at least a portion of the hollow glass body which has been separated.

10. The method according to claim 9,
wherein the receptacle is a medical receptacle.

11. The method according to claim 10, further comprising:
filling the medical receptacle with a formulation which comprises at least one pharmaceutically active substance or a pharmaceutical carrier substance.

12. A system for manufacturing a receptacle, the system comprising:
a laser unit having a focusing device for focusing a laser beam on a wall of a glass tube for laser cutting the glass tube to separate a hollow glass body from the glass tube; and
a device for causing a relative rotation between the glass tube and the laser beam during the laser cutting,
wherein the laser unit is configured to radiate the laser beam so as to comprise pulses with a repetition rate of 3 kHz to 30 kHz and a pulse-duty factor of between 5% to 35%.

13. The system according to claim 12, further comprising:
a control device for controlling the laser unit such that at least a zone of the wall of the glass tube is cut by laser sublimation cutting.

14. The system according to claim 13,
wherein the control device is configured to control a pulse length and a repetition rate using an open-loop control or a closed-loop control to cut at least the zone of the wall of the glass tube by the laser sublimation cutting.

15. The system according to claim 12,
wherein the focusing device is configured such that a Rayleigh length of the laser beam is equal to or smaller than a wall thickness of the glass tube.

16. The system according to claim 12,
wherein an energy density of the laser beam allows the hollow glass body to be separated from the glass tube without a mechanical introduction of a scratch.

17. The system according to claim 12, further comprising:
a drive unit for rotatingly driving the glass tube during the laser cutting.

18. The system according to claim 12, further comprising:
devices for holding and rotating glass tubes; and
a conveyor device on which the devices for holding and rotating the glass tubes are arranged.

19. The system according to claim 18, further comprising:
a drive unit for rotatingly driving the conveyor device.

20. The system according to claim 18, further comprising:
optical components for splitting the laser beam into a plurality of subbeams or deflecting the laser beam to cut the glass tubes on at least two of the devices for holding and rotating the glass tubes.

\* \* \* \* \*